United States Patent [19]
Rubsamen et al.

[11] Patent Number: 5,829,435
[45] Date of Patent: Nov. 3, 1998

[54] PREFILTER FOR PREVENTION OF CLOGGING OF A NOZZLE IN THE GENERATION OF AN AEROSOL AND PREVENTION OF ADMINISTRATION OF UNDESIRABLE PARTICLES

[75] Inventors: Reid Rubsamen, Berkeley; Igor Gonda, San Francisco; Stephen Farr, Orinda; David Cipolla, Belmont, all of Calif.

[73] Assignee: Aradigm Corporation, Hayward, Calif.

[21] Appl. No.: 804,041

[22] Filed: Feb. 24, 1997

[51] Int. Cl.$^6$ .......................... A61M 15/08; A61M 16/10; A61M 11/00
[52] U.S. Cl. ................................ 128/203.21; 128/200.14; 128/203.23
[58] Field of Search ........................ 128/200.14, 203.12, 128/203.21, 203.23, 203.28, 204.12

[56] References Cited

U.S. PATENT DOCUMENTS

| | | |
|---|---|---|
| 1,063,406 | 6/1913 | Witt . |
| 3,658,059 | 4/1972 | Steil . |
| 3,934,585 | 1/1976 | Maurice . |
| 4,677,975 | 7/1987 | Edgar et al. . |
| 5,404,871 | 4/1995 | Goodman et al. . |
| 5,419,315 | 5/1995 | Rubsamen . |
| 5,450,336 | 9/1995 | Rubsamen et al. . |
| 5,497,763 | 3/1996 | Lloyd et al. . |
| 5,497,944 | 3/1996 | Weston et al. . |
| 5,544,646 | 8/1996 | Lloyd et al. . |
| 5,647,349 | 7/1997 | Ohki et al. . |

FOREIGN PATENT DOCUMENTS

| | | |
|---|---|---|
| 2142246 | 1/1985 | United Kingdom . |
| WO 96/06581 | 3/1996 | WIPO . |
| WO 96/09846 | 4/1996 | WIPO . |
| WO 96/13290 | 5/1996 | WIPO . |
| WO 96/13292 | 5/1996 | WIPO . |

*Primary Examiner*—Kimberly L. Asher
*Attorney, Agent, or Firm*—Bozicevic & Reed LLP; Karl Bozicevic; Carol L. Francis

[57] ABSTRACT

A device, drug package and methodology for using such to generate an aerosol by moving a flowable formulation through a low resistance filter and then through a nozzle comprised of a porous membrane are disclosed. The package is comprised of a collapsible wall portion that forms a container for holding a liquid formulation which container has an opening covered by a cover portion comprising a nozzle. The membrane pores of the nozzle have a size in the range of 0.25 to 6 microns, preferably 0.5 to 6 microns. A low resistance filter, which is positioned between the flowable formulation and the nozzle, includes openings that are the same size as or smaller than the pores of the nozzle's porous membrane but includes the openings in an amount and density such that flowable formulation flows through the filter with less resistance than when the formulation moves through the porous membrane. Thus, the filter does not significantly increase the amount of pressure needed to aerosolize the formulation, prevents clogging of the porous membrane of the nozzle by any undesirable particles that may be in the formulation, prevents delivery of any such undesirable particles to the patient, and thereby improves the homogeneity of the aerosol formulation delivered to the patient, as well as the consistency and reproducibility of the aerosolized dose created.

40 Claims, 6 Drawing Sheets

PREFILTER FOR PREVENTION OF CLOGGING OF A NOZZLE IN THE GENERATION OF AN AEROSOL AND PREVENTION OF ADMINISTRATION OF UNDESIRABLE PARTICLES

FIELD OF THE INVENTION

This invention relates generally to devices and methods for aerosolizing formulations. More specifically, this invention relates to a low resistance filter used in the generation of aerosols of a desired aerosol particle size range, which can then be delivered to specific areas of the respiratory tract or eye.

BACKGROUND OF THE INVENTION

Aerosol therapy can be accomplished by aerosolization of a formulation (e.g., a drug formulation or diagnostic agent formulation) and inhalation of the aerosol. The formulation can be used to treat lung tissue locally and/or be absorbed into the circulatory system to deliver the drug systemically. Where the formulation contains a diagnostic agent, the formulation can be used for diagnosis of, for example, conditions and diseases associated with pulmonary dysfunction. In general aerosolized particles for respiratory delivery must have a diameter of 12 microns or less. However, the preferred particle size varies with the site targeted (e.g, delivery targeted to the bronchi, bronchia, bronchioles, alveoli, or circulatory system). For example, topical lung treatment can be accomplished with particles having a diameter in the range of 0.01 to 12.0 microns. Effective systemic treatment requires particles having a smaller diameter, generally in the range of 0.5 to 6.0 microns, while effective ocular treatment is adequate with particles having a larger diameter, generally in 15 microns or greater, generally in the range of 15–100 microns.

Generation of aerosolized particles and their respiratory delivery is generally accomplished by three distinct methodologies. One method use a device known as a "metered dose inhaler" (MDI). Drugs delivered using an MDI are dispersed in a low boiling point propellant (e.g., a chloroflurocarbon or hydroflurorcarbon) and loaded in a pressurized canister. A metered amount of the drug/propellant formulation is released from the MDI by activating a valve on the canister. The propellant "flashes" or quickly evaporates and particles of the drug are inhaled by the patient. Although MDIs provide a self-contained, easily portable device, the propellants have adverse environmental effects. In addition, MDIs can not be used to reliably deliver a precise dosage of drug. The patient frequently actuates the device at the incorrect point during the breathing cycle or breathes at the wrong flow rate while inhaling the drug. Thus, patients may inspire too little medication, or take a second dose and receive too much medication.

Breath actuated drug delivery devices, which attempt to overcome the dosing problems of MDIs, are activated to release a dose when the patient's inspiratory flow crosses a fixed threshold. However, the patient's inspiration effort may be sufficient to release a metered dose, but the inspiratory flow following the release may not be sufficient to cause the aerosol medication to pass into the desired portion of the patient's airways. Moreover, the patient's inspiratory effort may not be sufficient to satisfy the threshold to trigger drug release at all. Finally, whether breath-actuated or not, MDIs generate an aerosol that can contain particles of very different sizes. Larger particles are not delivered to the same site in the lung and/or at the same rate as the smaller particles in the aerosol. The production of an aerosol of varying particle size thus makes the delivery of a precise, reproducible dosage of medication or diagnostic agent to the desired regions of the respiratory tract extremely difficult if not impossible.

The second method for generation of aerosolized particles for respiratory delivery uses devices known as "dry powder inhalers" (DPI). DPIs typically use bursts of air to entrain small amounts of the drug, thus forming a dust cloud of dry drug particles. DPIs do not require the propellants of MDIs. However, like MDIs, DPIs form aerosols composed of many different sizes of particles, making the delivery of a precise dose to a desired site in the respiratory tract difficult.

Nebulizers, devices used in a third method of respiratory drug delivery, utilize various means to create a fog or mist from an aqueous solution or suspension containing a pharmaceutically active drug. The mist created by the nebulizer device is directed towards the face of the patient and inhaled through the mouth and/or nose. The formulation delivered with nebulizers are sometimes diluted prior to delivery. The entire diluted formulation must generally be administered within a single dosing event in order to maintain the desired level of sterility.

Nebulizer devices can be quite useful when the precise dosing of the drug being delivered to the patient is not of particular importance, e.g., for treatment of a patient with a bronchodilator until he feels some improvement in lung function. When precise dosing is more important, the nebulizer device and delivery methodology suffers from many of the disadvantages of metered dose inhaler devices and methodology as described above. In addition, nebulizers generally are large and not hand-held, easily transportable devices. Accordingly, a nebulizer can only be used within a fixed location such as the patient's home, the doctor's office and/or hospital. Yet another disadvantage of nebulizers is that they produce an aerosol which has a distribution of particle sizes, not all of which are of appropriate size to reach the targeted areas of the lung.

An aerosolation device can also be used to deliver treatment to the eye. Ophthalmic treatment fluids are commonly administered to the eye by means of eye drops of ointments. The use of eye drops has a number of disadvantages, primarily as a consequence of the difficulty with which drops are accepted by the patient. The drops are relatively large, and the instinctive blink that is provoked by the arrival of a drop on the eye severely limits the amount of or proportion of fluid that actually contacts the target area of the eye. Typically less than 10% of a 50 $\mu$l drop reaches the desired site of administration, the remainder being lost by drainage, either externally or through nasolacrimal drainage. Such use of expensive treatment fluids leads to substantial uncertainty regarding the effectiveness of treatment. Ointments are associated with similar problems in their use to accomplish ocular therapy.

Various techniques for delivering treatment fluid to the eye are known. Most employ treatment systems in which treatment fluid is drawn from a reservoir and discharged in a controlled manner to the eye (see, e.g., WO 96/06581). U.S. Pat. No. 3,934,585 discloses a variety of mechanisms for delivering unit doses of treatment fluid to the human eye. For example, treatment fluid can be delivered by applying compressed air to one end of a tube resulting in the discharge of treatment fluid from the other end.

Devices and methods for controlling aerosol particle size are known in the art. For example, U.S. Pat. No. 4,926,852 describes control of particle size by metering a dose of medication into a flow-through chamber that has orifices to limit the flow rate. U.S. Pat. No. 4,677,975 describes a nebulizer device that uses baffles to remove particles above a selected size from an aerosol. U.S. Pat. No. 3,658,059 refers to a baffle that changes the size of an aperture in the passage of the suspension being inhaled to select the quantity and size of suspended particles delivered. U.S. Pat. No. 5,497,944 describes a method and device for generating an aerosol by passing the formulation through a small nozzle aperture at high pressure. Devices that process the aerosol particle size after it is generated (e.g., by filtering the aerosol after it is formed from the formulation) are inefficient, wasteful, and/or require a substantially greater amount of force to generate the aerosol.

SUMMARY OF THE INVENTION

A device, drug package and methodology for using such to generate an inhalable or externally applicable aerosol by moving a flowable formulation through a low resistance filter and a nozzle, which nozzle is comprised of a porous membrane, are disclosed. The low-resistance filter and nozzle can be used with either the disposable packages of the invention or with multidose containers. The package is comprised of a collapsible wall portion that forms a container for holding a liquid formulation which container has an opening covered by a cover portion comprising a nozzle. For administration of drug to the respiratory tract, the membrane pores of the nozzle's porous membrane have a size in the range of 0.25 to 6 microns, preferably 0.5 to 5 microns. For administration of drug to the eye the membrane pores of the nozzle's porous membrane have a size in the range of 5 to 50 microns, preferably 7.5 to 25 microns. A low resistance filter is positioned between the liquid formulation and the nozzle. The filter preferably has a porosity such that liquid formulation flows through the filter with less resistance than when the liquid moves through the nozzle. Thus, the filter does not significantly increase the amount of pressure needed to aerosolize the formulation and greatly reduces the probability of clogging the nozzle thereby improving the consistency in the aerosolized dose created.

The invention also features a disposable drug package for use in generating an inhalable or externally applicable aerosol for respiratory therapy (e.g., involving nasal and/or intrapulmonary delivery) or for delivery of a diagnostic agent(s).

One object of the invention is to provide a method for generating an aerosol using a low resistance filter to prevent clogging of the nozzle's porous membrane by particulate matter that may be present in the formulation as a result of the presence of contaminants during formulation production or formulation packaging, or that may have formed in the formulation upon standing.

Another object of the invention is to generate an aerosol from the flowable formulation contained in the disposable package such that the generated aerosol is composed of particles of a desired size and does not contain any undesirable particulate matter (e.g., undissolved particles of drug or diagnostic agent or other formulation component, microorganisms, or other matter that may be present in the formulation and that is undesirable for delivery to a patient).

Another object of the invention is to enhance the safety and suitability of the drug formulation for inhalation by a patient or delivery to a patient's eye by using a low resistance filter to prevent microorganisms and other harmful particles accidentally present in a formulation from being delivered to the patient in the aerosol.

Another object of the invention is to facilitate delivery of the drug to particular areas of the respiratory tract by adjusting particle size by passing the drug formulation through a low resistance filter having pores of a desired size and a desired porosity and then through a nozzle comprised of a porous membrane having pores of a desired size, thereby producing an aerosol composed primarily of particles having a desired diameter or range of diameters.

Another advantage of the invention is that extrusion of the formulation through the low resistance filter and the porous membrane of the nozzle to create an aerosol does not require high pressure, requiring a pressure of about 50 bar or less, generally 35 bar or less.

Another advantage of the invention is that the package can be used with a breath actuated, motor driven device that is capable of applying the necessary low pressure to the package to extrude the formulation and generate an aerosol.

Another object of this invention to provide a method of aerosolized delivery of a drug formulation or a diagnostic agent in a safe, reproducible and effective manner.

An advantage of the present invention is that it can be used for ambulatory patients with respiratory disease.

Another advantage of the present invention is that it can be used to provide reproducible dosing in ocular treatment.

These and other objects, advantages and features of the present invention will become apparent to those skilled in the art upon reading this disclosure in combination with drawings wherein like numerals refer to like components throughout.

DETAILED DESCRIPTION OF THE PREFERRED EMBODIMENTS

Figure 1:
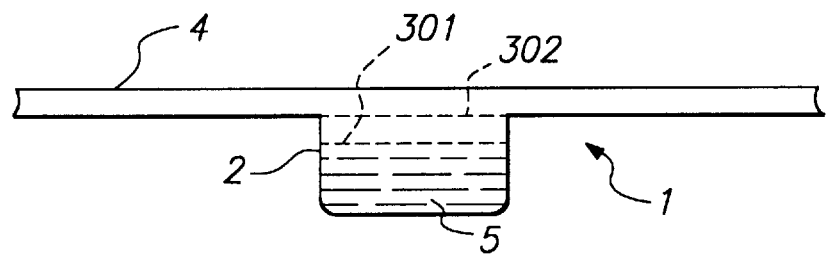
FIG. 1 is a cross-sectional view of a container used in carrying out the invention.

Before the present methods of generating an aerosol and delivering an aerosolized formulation to a patient and devices, containers, and formulations used in connection with such are described, it is to be understood that this invention is not limited to the particular methodology, devices, containers and formulations described, as such methods, devices, containers and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an asthma attack" includes one or more of such events, and reference to "the method of treatment" and to "the method of diagnosis" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The publications discussed above are provided solely for their disclosure prior to the filing date of the present application. Nothing herein is to be construed as an admission that the invention is not entitled to antedate such disclosure by virtue of prior invention.

Definitions

The terms "package" and "disposable package" are used interchangeably herein and shall be interpreted to mean a container or two or more containers linked together by an interconnecting means wherein each container preferably includes one or more channels which provide for fluid connection from the container to a nozzle comprised of a porous membrane, which nozzle is preferably not positioned directly over the container, and wherein each container includes at least one surface that is collapsible in a manner so as to allow the forced displacement of the contents of the container through a low resistance filter and out of the nozzle (without rupturing the container) in a manner such that the contents is aerosolized. There are at least two variations of the package, depending on whether the drug can be stably stored in a liquid form or must be stored dry and combined with liquid immediately prior to aerosolization.

The contents of each container preferably comprises a formulation, preferably a flowable formulation, more preferably a liquid, flowable formulation, which includes a pharmaceutically active drug or a diagnostic agent. If the drug or diagnostic agent is not liquid and of a sufficiently low viscosity to allow the drug to be aerosolized, the drug or diagnostic agent is dissolved or dispersed in an excipient carrier, preferably without any additional material such as preservatives that might affect the patient. When the contents must be stored in a dry state, the package further includes another container that holds the liquid and can be combined with the dry drug immediately prior to administration.

The term "container" is used herein to mean a receptacle for holding and/or storing a drug formulation. The container can be single-dose or multidose, and/or disposable or refillable.

The term "cassette" shall be interpreted to mean a container which holds, in a protective cover, a package or a plurality of packages which packages are interconnected to each other and held in the cassette in an organized manner, e.g., interfolding or wound. The cassette is connectable to a dispensing device, which dispensing device may include a power source, e.g., one or more batteries which provide power to the dispensing device.

The term "porosity" is used herein to mean a percentage of an area of a surface area that is composed of open space, e.g., a pore or other opening, in a membrane or filter. The percent porosity is thus defined as the total area of open space divided by the area of the filter, expressed as a percentage (multiplied by 100). High porosity (e.g., a porosity greater than 50%) is associated with high flow rates per unit area and low flow resistance. In general, the porosity of the nozzle is less than 10%, and can vary from $10^{-3}$% to $10^{-1}$%, while the porosity of the filter is at least 1%, and preferably it is at least 50% porous.

The term "porous membrane" shall be interpreted to mean a membrane of material having any given outer parameter shape, but preferably having a convex shape, wherein the membrane has a plurality of pores therein, which openings may be placed in a regular or irregular pattern, and which pores have a diameter in the range of 0.25 micron to 6 microns and a pore density in the range of 1 to 1,000 pores per square millimeter for respiratory delivery. For ocular delivery, the pores have a diameter in the range of 5 microns to 50 microns, preferably 7.5 to 25 microns, and a similar pore density. The porous membrane has a porosity of about 0.0005% to 0.2%, preferably about 0.01% to 0.1%. In one embodiment, the porous membrane comprises a single row of pores on, e.g., a large piece of membrane material. The pores may be planar with respect to the surface of the porous membrane material, or may have a conical configuration. The membrane material is preferably hydrophobic and includes materials such as polycarbonates and polyesters which may have the pores formed therein by any suitable method including laser drilling or anisotropic etching through a thin film of metal or other suitable material. The membrane preferably has sufficient structural integrity so that it is maintained intact (will not rupture) when subjected to force in the amount up to about 35 bar, preferably of up to about 50 bar while the formulation is forced through the pores.

The term "low resistance filter" shall be interpreted to mean a filter of material having any given outer parameter shape, and having a plurality of openings therein, which openings may be placed in a regular or irregular pattern. The openings in the filter can be of any shape, and are preferably substantially evenly distributed throughout the filter surface area. Preferably, the porosity of the low resistance filter is greater than 50%, preferably at least 60%, more preferably at least 70%. Preferably, the low resistance filter prevents passage of particles greater than about 0.5 microns in size (e.g., having a diameter greater than 0.5 microns). Where the filter openings are pores, the pores can have a diameter in the range of from about 0.25 micron to 6 microns for respiratory tract delivery, or from about 5 microns to 50 microns for ocular delivery. The filter has an opening density in the range of from about 10 to 20,000,000 openings per $mm^2$. Preferably the filter has holes of about 0.5 $\mu$m positioned about 0.5 $\mu$m apart at a density of $10^6$ holes per $mm^2$. Preferably, the ratio of the pore density of the porous membrane to the low resistance filter is in the range of about 1:1.5 to about 1:100,000; the ratio of the pore diameter of the pores of the porous membrane to the diameter of the openings of the low resistance filter is in the range of from about 1:0.95 to 1:0.1. Preferably, the flow resistance of the filter is the same as or lower than the flow resistance of the porous membrane used in conjunction with the filter. The filter is preferably comprised of a material having a density in the range of 0.25 to 3.0 mg/cm$^2$, more preferably 1.7 mg/cm$^2$, and a thickness of about 10 microns to about 500 microns, more preferably about 20 to 150 microns. The filter can be made of any material suitable for use in the invention, e.g., cellulose ester, mixed cellulose ester, modified polyvinylidene fluoride, polytetrafluoroethylene, bisphen polycarbonate, borosilicate glass, silver, polypropylene, polyester, polyimide, polyether, or any suitable polymeric material. The filter material includes materials such as polycarbonates and polyesters which may have the pores formed therein by any suitable method, including anisotropic etching or by etching through a thin film of metal or other suitable material, electron discharge machining, or laser micromachining. The filter preferably has sufficient structural integrity such that it is maintained intact (i.e., will not rupture) when subjected to force up to about 35 bar, preferably up to about 50 bar during extrusion of the formulation through the pores. The porosity of the low resistance filter is 5–85%, preferably 70%, while the porosity of the nozzle is $10^{-4}\%$–1%, preferably 0.001%–0.1%.

The term "flow resistance" shall be interpreted to mean the resistance associated with the passage of a liquid or aerosol through a porous material, e.g., through the porous membrane or the low resistance filter described herein. Flow resistance is affected by the size and density of pores in the porous material, the viscosity of a liquid passing through the material, and other factors well known in the art. In general, "low resistance" of the "low resistance filter" means that the flow resistance of the low resistance filter is substantially the same as or less than the flow resistance of the porous membrane used in conjunction with the low resistance filter.

The terms "drug" and "pharmaceutically active drug" and the like are used interchangeably herein to encompass compounds which are administered to a patient in order to obtain a desired pharmacological effect. The effect may be a local or topical effect in the eye or respiratory tract such as in the case of most respiratory or ophthalmic drugs or may be systemic as with analgesics, narcotics, hormones, hematopoietic drugs, various types of peptides including insulin and hormones such as EPO. Other exemplary drugs are set forth in U.S. Pat. No. 5,419,315, issued May 30, 1995, PCT Published Application WO 96/13291, published May 9, 1996, and PCT Published Application WO 96/13290, published May 9, 1996, incorporated herein by reference.

The term "respiratory drug" shall be interpreted to mean any pharmaceutically effective compound used in the treatment of any respiratory disease and in particular the treatment of diseases such as asthma, bronchitis, emphysema and cystic fibrosis. Useful "respiratory drugs" include those which are listed within the Physician's Desk Reference (most recent edition). Such drugs include beta adrenergic agonists which include bronchodilators including albuterol, isoproterenol sulfate, metaproterenol sulfate, terbutaline sulfate, pirbuterol acetate, salmeterol xinotoate, formoteorol; steroids including corticosteroids used as an adjunct to beta agonist bronchodilators such as beclomethasone dipropionate, flunisolide, fluticasone, budesonide and triamcinolone acetonide; and also includes peptide nonadrenergic noncholinergic neurotransmitters and anticholinergics. Antiinflammatory drugs used in connection with the treatment of respiratory diseases include steroids such as beclomethasone dipropionate, triamcinolone acetonide, flunisolide and fluticasone. Other antiinflammatory drugs and antiasthmatics which include cromoglycates such as cromolyn sodium. Other respiratory drugs which would qualify as bronchodilators include anticholinergics including ipratropium bromide. Other useful respiratory drugs include leukotriene (LT) inhibitors, vasoactive intestinal peptide (VIP), tachykinin antagonists, bradykinin antagonists, endothelin antagonists, heparin furosemide, antiadhesion molecules, cytokine modulators, biologically active endonucleases, recombinant human (rh) DNase, $\alpha_1$ antitrypsin and antibiotics such as gentamicin, tobramycin, cephalosporins or penicillins, nucleic acids and gene vectors. The present invention is intended to encompass the free acids, free bases, salts, amines and various hydrate forms including semihydrate forms of such respiratory drugs and is particularly directed towards pharmaceutically acceptable formulations of such drugs which are formulated in combination with pharmaceutically acceptable excipient materials generally known to those skilled in the art—preferably without other additives such as preservatives. Preferred drug formulations do not include additional components such as preservatives which have a significant effect on the overall formulation. Thus preferred formulations consist essentially of pharmaceutically active drug and a pharmaceutically acceptable carrier (e.g., water and/or ethanol). However, if a drug is liquid without an excipient the formulation may consist essentially of the drug which has a sufficiently low viscosity that it can be aerosolized using a dispenser of the present invention.

The term "ophthalmic drug" or "ophthalmic treatment fluid" refers to any pharmaceutically active compound used in the treatment of any ocular disease. Therapeutically useful compounds include, but are not limited to, (1) antiglaucoma compounds and/or compounds that decrease intraocular pressure such as β-adrenoceptor antagonists (e.g., cetamolol, betaxolol, levobunolol, metipranolol, timolol, etc.), mitotics (e.g., pilocarpine, carbachol, physostigmine, etc.), sympatomimetics (e.g., adreniline, dipivefrine, etc.), carbonic anhydrase inhibitors (e.g., acetazolamide, dorzolamide, etc.), prostaglandins (e.g., PGF-2 alpha), (2) antimicrobal compounds including antibacterial and antifungal compounds (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines, etc., (3) antiviral compounds (e.g., acyclovir, cidofovir, idoxuridine, interferons, etc.), (4) aldose reductase inhibitors (e.g., tolrestat, etc.), (5) antiinflammatory and/or antiallergy compounds (e.g., steroidal compounds such as betamethasone, clobetasone, dexamethasone, fluorometholone, hydrocortisone, prednisolone, etc. and nonsteroidal compounds such as antazoline, bromfenac, diclofenac, indomethacin, lodxamide, saprofen, sodium cromoglycate, etc., (6) artificial tear/dry eye therapies, comfort drops, irrigation fluids, etc. (e.g., physiological saline, water, or oils; all optionally containing polymeric compounds such as acetylcysteine, hydroxyethylcellulose, hydroxymellose, hyaluronic acid, polyvinyl alcohol, polyacrylic acid derivatives, etc.), (7) local anaesthetic compounds (e.g., amethocaine, lignocaine, oxbuprocaine, proxymetacaine, etc.), (8) compounds which assist in the healing of corneal surface defects (e.g., cyclosporine, diclofenac, urogastrone and growth factors such as epidermal growth factor), (9) mydriatics and cycloplegics (e.g., atropine, cyclopentolate, homatropine, hyoscine, tropicamide, etc.), (10) compounds for the treatment of pterygium (e.g., mitomycin C., collagenase inhibitors such as batimastat, etc.), (11) compounds for the treatment of macular degeneration and/or diabetic retinopathy and/or cataract prevention, (12) compounds for systemic effects following absorption into the bloodstream after ocular administration (e.g., insulin, narcotics, analgesics, anesthetics).

The terms "diagnostic" and "diagnostic agent" and the like are used interchangeably herein to describe any compound that is delivered to a patient in order to carry out a diagnostic test or assay on the patient. Such agents are generally tagged with a radioactive or fluorescent component or other component which can be readily detected when administered to the patient. Exemplary diagnostic agents include, but are not limited to, methacholine, histamine, salt, specific allergens (such as pollen or pollen extracts), sulphites, and imaging agents for magnetic resonance imaging and/or scintigraphy. Diagnostic agents can be used to, for example, assess bronchial constriction in patients having or suspected of having cystic fibrosis or asthma. Radiolabelled aerosols can be used to diagnose pulmonary embolism, or to assess mucociliary clearance in various chronic obstructive diseases of the lung. Diagnostic agents can also be used to assess ophthalmic conditions. Exemplary ocular diagnostic agents include, but are not limited to, such compounds as fluorescein or rose bengal.

The term "formulation" is intended to encompass any drug or diagnostic agent formulation which is delivered to a patient using the present invention. Such formulations generally include the drug or diagnostic agent present within a pharmaceutically acceptable inert carrier. The formulation is generally in a liquid flowable form which can be readily aerosolized, the particles having a particle size in the range of 0.5 to 10 microns in diameter. Formulations can be administered to the patient using device of the invention can be administered by nasal, intrapulmonary, or ocular delivery.

The terms "aerosol," "aerosolized formulation," and the like, are used interchangeably herein to describe a volume of air which has suspended within it particles of a formulation comprising a drug or diagnostic agent wherein the particles have a diameter in the range of 0.5 to 12 microns, for respiratory therapy, or in the range of 15 to 50 microns for ocular therapy.

The term "aerosol-free air" is used to describe a volume of air which is substantially free of other material and, in particular, substantially free of particles of respiratory drug.

The term "dosing event" shall be interpreted to mean the administration of drug or diagnostic agent to a patient by the ocular or respiratory (e.g., nasal or intrapulmonary) route of administration (i.e., application of a formulation to the patient's eye or to the patient's respiratory tract by inhalation of aerosolized particles) which event may encompass one or more releases of drug or diagnostic agent formulation from a dispensing device over a period of time of 15 minutes or less, preferably 10 minutes or less, and more preferably 5 minutes or less, during which period multiple administrations (e.g., applications to the eye or inhalations) may be made by the patient and multiple doses of drug or diagnostic agent may be released and administered. A dosing event shall involve the administration of drug or diagnostic formulation to the patient in an amount of about 10 $\mu$l to about 1,000 $\mu$l in a single dosing event. In that the drug or diagnostic agent is dissolved in a carrier to form the formulation, the amount of drug or diagnostic agent delivered may be very small and will vary with the concentration of drug or diagnostic agent in the carrier. Accordingly, a dosing event may include the release of drug or diagnostic agent contained within one of many containers of a package held in a cassette or the drug or diagnostic agent contained within a plurality of such containers when the containers are administered over a period of time, e.g., within 5 to 10 minutes of each other, preferably within 1–2 minutes of each other.

The term "velocity of the drug" or "velocity of particles" shall mean the average speed of particles of drug or diagnostic agent formulation moving from a release point such as the porous membrane of the nozzle or a valve to a patient's mouth or eye. In a preferred embodiment pertaining to respiratory therapy, the relative velocity of the particles is zero or substantially zero with reference to the flow created by patient inhalation.

The term "bulk flow rate" shall mean the average velocity at which air moves through a channel.

The term "flow boundary layer" shall mean a set of points defining a layer above the inner surface of a channel through which air flows wherein the air flow rate below the boundary layer is substantially below the bulk flow rate, e.g., 50% or less than the bulk flow rate.

The term "carrier" shall mean a flowable, pharmaceutically acceptable excipient material, preferably a liquid, flowable material, in which a drug or diagnostic agent is suspended in or more preferably dissolved in. Useful carriers do not adversely interact with the drug or diagnostic agent and have properties which allow for the formation of aerosolized particles, which particles preferably have a diameter in the range of 0.5 to 12.0 microns that are generated by forcing a formulation comprising the carrier and drug or diagnostic agent through pores having a diameter of 0.25 to 6.0 microns for delivery to the respiratory tract. Similarly, a useful carrier for delivery to the eye does not adversely interact with the drug or diagnostic agent and has properties which allow for the formation of aerosolized particles, which particles preferably have a diameter of 15 to 50 microns and are generated by forcing the formulation comprising the carrier and drug or diagnostic agent through pores 7.5 to 25 microns in diameter. Preferred carriers include water, ethanol, saline solutions and mixtures thereof with pure water being preferred. Other carriers can be used provided that they can be formulated to create a suitable aerosol and do not adversely affect human tissue or the drug or diagnostic agent to be delivered.

The term "measuring" describes an event whereby the (1) total lung capacity, (2) inspiratory flow rate or (3) inspiratory volume of the patient is measured and/or calculated and the information used in order to determine an optimal point in the inspiratory cycle at which to release an aerosolized and/or aerosol-free volume of air. An actual measurement of both rate and volume may be made or the rate can be directly measured and the volume calculated based on the measured rate. The total lung capacity can be measured or a calculated based on the patient's height, sex and age. It is also preferable to continue measuring inspiratory flow during and after any drug delivery and to record inspiratory flow rate and volume before, during and after the release of drug. Such reading makes it possible to determine if drug or diagnostic agent was properly delivered to the patient.

The term "monitoring" shall mean measuring lung functions such as inspiratory flow, inspiratory flow rate, and/or inspiratory volume so that a patient's lung function as defined herein, can be evaluated before and/or after drug delivery thereby making it possible to evaluate the effect of drug delivery on, for example, the patient's lung function.

The term "inspiratory flow profile" shall be interpreted to mean data calculated in one or more events measuring inspiratory flow and cumulative volume, which profile can be used to determine a point within a patient's inspiratory cycle which is optimal for the release of drug to be delivered to a patient. An optimal point within the inspiratory cycle for the release of an aerosol volume is based, in part, on (1) a point most likely to deliver the aerosol volume to a particular area of a patient's respiratory tract, in part on (2) a point within the inspiratory cycle likely to result in the maximum delivery of drug and, in part, on (3) a point in the cycle most likely to result in the delivery of a reproducible amount of drug to the patient at each release of drug. The criteria 1–3 are listed in a preferred order of importance. However, the order of importance can change based on circumstances. The area of the respiratory tract being treated is determined by adjusting the volume of aerosol-containing or aerosol-free air and/or by adjusting the particle size of the aerosol. The repeatability is determined by releasing at the same point in the respiratory cycle each time drug is released. To provide for greater efficiency in delivery, the drug delivery point is selected within given parameters.

The terms "formulation" and "flowable formulation" and the like are used interchangeably herein to describe any pharmaceutically active drug (e.g., a respiratory drug, or drug that acts locally or systemically, and that is suitable for respiratory delivery) or diagnostic agent combined with a pharmaceutically acceptable carrier in flowable form having properties such that it can be aerosolized to particles having a diameter of 0.5 to 12.0 microns for respiratory therapy, or 15 to 75 microns for ocular therapy. Such formulations are preferably solutions, e.g., aqueous solutions, ethanolic solutions, aqueous/ethanolic solutions, saline solutions, colloidal suspensions and microcrystalline suspensions. Preferred formulations are drug(s) and/or diagnostic agent(s) dissolved in a liquid, preferably in water.

The term "substantially dry" shall mean that particles of formulation include an amount of carrier (e.g., water or ethanol) which is equal to (in weight) or less than the amount of drug or diagnostic agent in the particle, more preferably it means free water is not present.

The terms "aerosolized particles" and "aerosolized particles of formulation" shall mean particles of formulation comprised of carrier and drug and/or diagnostic agent that are formed upon forcing the formulation through a nozzle, which nozzle comprises a flexible porous membrane. Where respiratory therapy is desired, the particles are of a sufficiently small size such that when the particles are formed, they remain suspended in the air for a sufficient amount of time for inhalation by the patient through his nose or mouth. Where ocular therapy is desired, the particles formed are of a size optimal for application to the eye. Preferably, particles for respiratory delivery have a diameter of from about 0.5 micron to about 12 microns, and are generated by forcing the formulation through the pores of a flexible porous membrane, where the pores have a diameter in the range of about 0.25 micron to about 6.0 microns. More preferably, the particles for respiratory delivery have a diameter of about 1.0 to 8.0 microns with the particles created by being moved through pores having a diameter of about 0.5 to about 4 microns. For ocular delivery, the articles' diameter is from about 15 micron to about 75 microns, and are generated by forcing the formulation through the pores of a flexible porous membrane, where the pores have a diameter in the range of about 5 micron to about 50 microns. More preferably, the particles for ocular delivery have a diameter of about 15 to 50 microns, and can be generated by forcing the formulation through flexible membrane pores having a diameter of about 7.5 to about 25 microns. In either respiratory or ocular delivery, the flexible membrane pores are present at about 10 to 10,000 pores over an area in size of from about 1 sq. millimeter to about 1 sq. centimeter, preferably from about $1 \times 10^1$ to about $1 \times 10^4$ pores per square millimeter, more preferably from about $1 \times 10^2$ to about $3 \times 10^4$ pores per square millimeter, and the low resistance filter has an opening density in the range of 20 to 1,000,000 pores over an area of about one square millimeter.

General Overview of the Methodology of the Invention

The invention provides a means to deliver any type of drug or diagnostic agent to a patient by ocular administration or inhalation in the form of an aerosol having a desired aerosol particle size and having substantially no undesirable particles within the aerosol that would substantially affect the accuracy of the dose of drug or diagnostic agent delivered in the aerosol. The method of generating an aerosol according to the invention provides a means to generate a reproducible desirable dose of aerosol for therapeutic and diagnostic applications. Moreover, certain embodiments of the devices and methodology used do not require the release of low boiling point propellants in order to aerosolize drug, which propellants are conventionally used in connection with hand-held metered dose inhalers. However, like conventional hand-held metered dose inhalers, the devices used in conjunction with the present invention can be hand-held, self-contained, highly portable devices which provide a convenient means of delivering drugs or diagnostic agents to a patient via the respiratory route.

In general, an aerosol for respiratory or ocular delivery is generated from a drug or diagnostic agent formulation, preferably a flowable formulation, more preferably a liquid, flowable formulation. The drug or diagnostic agent formulation can be contained within a multidose container or within a container portion of a disposable package, where the container of the disposable package has at least one surface that is collapsible. The aerosol is generated by applying pressure of 50 bar or less, preferably 35 bar or less, to the collapsible container surface, thereby forcing the contents of the container through a low resistance filter and then through a nozzle comprised of a porous membrane. The porous membrane may be rigid or flexible. Preferably the porous membrane is flexible so that upon application of the pressure required to aerosol the formulation (i.e., preferably 50 bar or less, more preferably 35 bar or less), the nozzle's porous membrane becomes convex in shape, thus delivering the aerosolized drug or diagnostic agent into the flow path of the delivery device in a region beyond the flow boundary layer. The low resistance filter has a porosity the same as or greater than the porosity of the porous membrane to provide for an overall flow resistance that is the same as the flow resistance of the nozzle. The low resistance filter thus prevents particles of an undesirable size from reaching the nozzle, thereby avoiding clogging of the nozzle, and filters out such undesirable particles before the aerosol for delivery is generated, thereby avoiding delivery of undesirable particles to the patient.

The formulations for use in the present invention can include preservatives or bacteriostatic type compounds. However, the formulation preferably comprises a pharmaceutically active drug (or a diagnostic agent) and pharmaceutically acceptable carrier. The formulation can be primarily or essentially composed of the drug or diagnostic agent (i.e., without carrier) if the drug or diagnostic agent is freely flowable and can be aerosolized. Useful formulations can comprise formulations currently approved for use with nebulizers.

Further the dispensing device of the present invention, which can be used to dispense a drug or diagnostic agent formulation according to the method of the invention, preferably includes electronic and/or mechanical components which eliminate direct user actuation of drug release. More specifically, where the device is used in respiratory therapy, the device preferably includes a means for measuring inspiratory flow rate and inspiratory volume and sending an electrical signal as a result of the simultaneous measurement of both (so that drug or diagnostic agent can be released at a preprogrammed optimal point) and also preferably includes a microprocessor which is programmed to receive, process, analyze and store the electrical signal of the means for measuring flow and upon receipt of signal values within appropriate limits sending an actuation signal to the mechanical means which causes drug (or diagnostic agent) to be extruded from the pores of the nozzle's porous membrane. Thus, since preferred embodiments of the devices used in connection with the present invention include a means of analyzing breath flow and a microprocessor capable of making calculations based the inhalation profile, the present invention can provide a means for repeatedly (1) dispensing and (2) delivering the same amount of the drug or diagnostic agent to a patient at each dosing event.

The present invention includes at least six distinct aspects which include (1) a disposable package, (2) a cassette which includes a plurality of packages, (3) a dispensing device which can be loaded with a cassette, (4) a delivery device that can be loaded with a ribbon of low resistance filters and/or a ribbon of porous membranes and used in conjunction with a disposable package or a multidose container, (5) a method of generating an aerosol and (6) a method of delivery of a drug or diagnostic agent.

The invention will now be described in more detail.

Low Resistance Filter, Nozzle, and Container Configurations of the Invention

In general, the low-resistance filter and nozzle comprised of a porous membrane according to the invention can be used in conjunction with any container suitable for containing a drug or diagnostic agent formulation of interest. The container can be, for example, a single-dose container or a multidose container. The containers can be refillable, reusable, and/or disposable. Preferably, the container is disposable. The container can be designed for storage and delivery of a drug or diagnostic agent that is dry, substantially dry, liquid, or in the form of a suspension. The container may be any desired size. In most cases the size of the container is not directly related to the amount of drug or diagnostic agent being delivered in that most formulations include relatively large amounts of excipient material, e.g., water or a saline solution. Accordingly, a given size container could include a wide range of different doses by varying drug (or diagnostic agent) concentration.

The container can also be one that provides for storage of a drug or diagnostic agent in a dry or substantially dry form until the time of administration, at which point, if desired, the drug or diagnostic agent can be mixed with water or other liquid. An exemplary dual compartment container for carrying out such mixing of dry drug with liquid just prior to administration is described in copending U.S. application Ser. No. 08/549,295, filed Oct. 27, 1995, incorporated herein by reference with respect to such containers.

In a preferred embodiment, the containers useful with the invention comprise a single-use, single-dose, disposable container that holds a formulation for delivery to a patient and having a collapsible wall. In addition, the container can be configured in the same package with a porous membrane and a low resistance filter, where the low resistance filter is positioned between the porous membrane and a formulation contained in the container. The container is preferably disposable after a single use in the delivery of the formulation contained therein.

FIG. 1 is a cross-sectional view of a disposable container 1 of the invention which is shaped by a collapsible wall 2.

The container 1 has an opening covered by a nozzle 302 comprised of a flexible porous membrane which is covered by a removable layer 4. The porous membrane of the nozzle 302 may be rigid and protrude upward in a convex configuration away from the formulation 5. A low resistance filter 301 is positioned between the formulation 5 and the nozzle 302. The filter 301 has a porosity such that the presence of the filter 301 does not substantially increase the pressure required to generate an aerosol by forcing the formulation through the porous membrane of the nozzle. When the layer 4 is removed the wall 2 can be collapsed thereby forcing the drug or diagnostic agent formulation 5 through the low resistance filter 301 and through the flexible porous membrane of the nozzle 302 which will then protrude outward in a convex shape.

Figure 2:
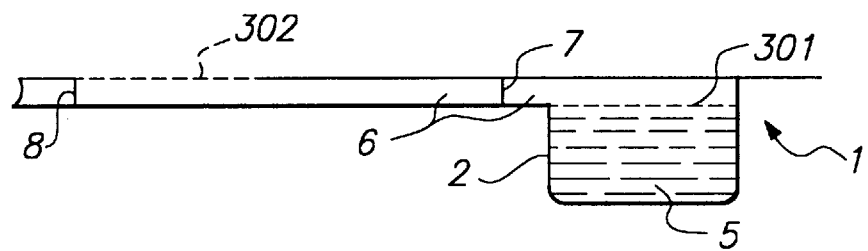
FIG. 2 is a cross-sectional view of a preferred embodiment of a container used in carrying out the invention.

FIG. 2 is a cross-sectional view of a more preferred embodiment of a disposable container 1 of the invention. The container is shaped by a collapsible wall 2. The container 1 includes an opening which leads to an open channel 6 which channel 6 includes an abutment (or burstable seal) 7 which is broken upon the application of force created by formulation 5 being forced from the container. The low resistance filter 301 is positioned between the formulation 5 and the burstable seal 7. When the abutment 7 is broken the formulation 5 flows to an area adjacent to the nozzle's flexible porous membrane 3 and is prevented from flowing further in the channel 6 by a nonbreakable abutment 8.

Figure 3:
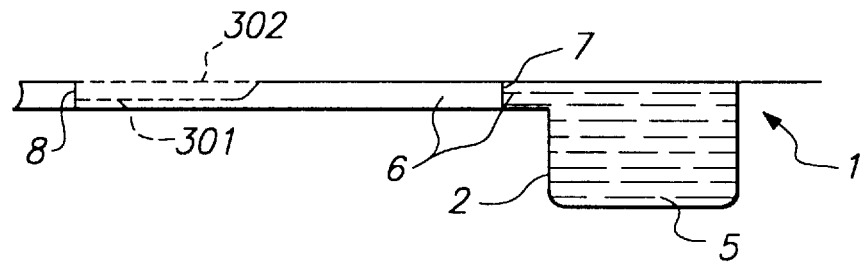
FIG. 3 is a cross-sectional view of a container of a preferred embodiment of a container used in carrying out the invention.
Figure 4:
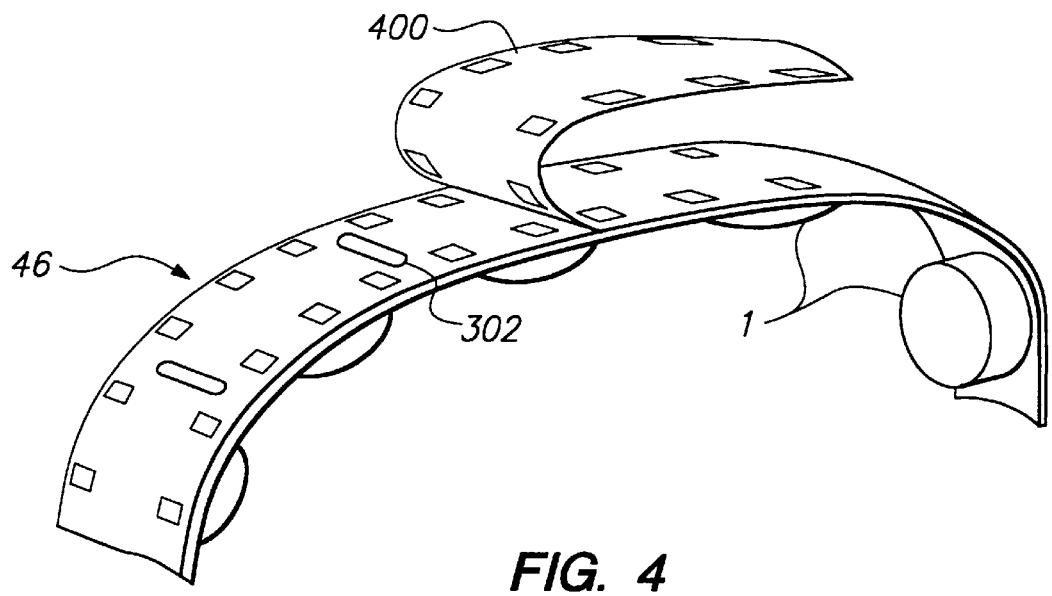
FIG. 4 is a top plan view of a disposable package of the invention.

FIG. 3 is a cross-sectional view of another preferred embodiment of a disposable container 1 of the invention. The container is shaped by a collapsible wall 2. The container 2 includes an opening which leads to an open channel 6, which channel 6 includes an abutment (or burstable seal) 7 which is broken upon the application of force created by formulation 5 being forced from the container. The low resistance filter 301 is positioned between the burstable seal 7 and the nozzle 302. When the burstable seal 7 is broken, the formulation 5 flows to an area adjacent the low resistance filter 301, through the low resistance filter 301, and out the nozzle 302 to form an aerosol. The formulation 5 is prevented from flowing further in the channel 6 by a nonbreakable abutment 8. A number of containers can be connected together to form a package 46 as shown in FIG. 4. The package 46 is shown in the form of an elongated tape, but can be in any configuration (e.g., circular, square, rectangular, etc.).

Figure 6:
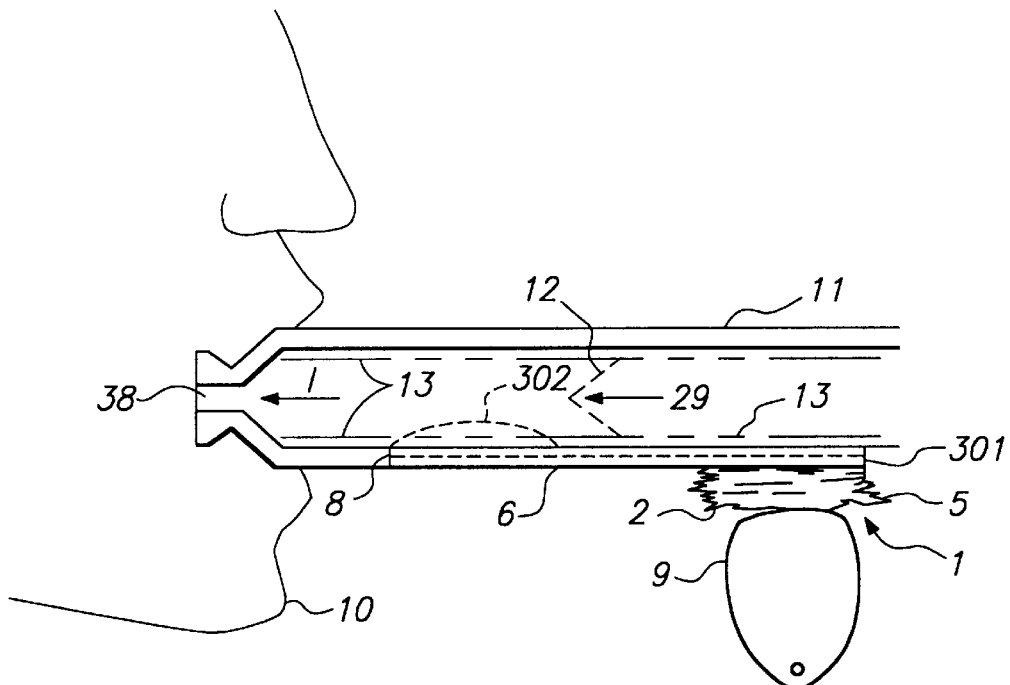
FIG. 6 is a cross-sectional view of the container of FIG. 2 in use in a channel of an aerosol delivery device.

FIG. 6 is a cross-sectional view of the disposable container 1 of FIG. 2 in use for respiratory therapy. The wall 2 is being crushed by a mechanical component such as the cam 9 shown in FIG. 3. The cam may be driven by a motor connected to gears which turn the cam 9 to bring the cam into contact with and apply the necessary force to the collapsible wall 2 of the container 1. The formulation 5 is forced through the low resistance filter 301, into the open channel 6 (breaking the abutment 7 shown in FIG. 2), and against and through the nozzle 302 causing the porous membrane of the nozzle 302 to protrude outward into a convex configuration as shown in FIG. 3. The cam 9 has been forced against the container wall 2 after a patient 10 begins inhalation in the direction of the arrow "I."An exemplary method for using the aerosol delivery device 40 is as follows. The patient 10 inhales through the mouth from a tubular channel 11. The velocity of the air moving through the flow path 29 of the channel 11 can be measured across the diameter of the channel to determine a flow profile 12, i.e., the air flowing through the channel 11 has a higher velocity further away from the inner surface of the channel. The air velocity immediately adjacent to the inner surface of the channel 11 (i.e., infinitely close to the surface) is very slow (i.e., approaches zero). A flow boundary layer 13 defines a set of points below which (in a direction from the channel center toward the inner surface of the channel) the flow of air is substantially below the bulk flow rate, i.e., 50% or less than the bulk flow rate.

Figure 5:
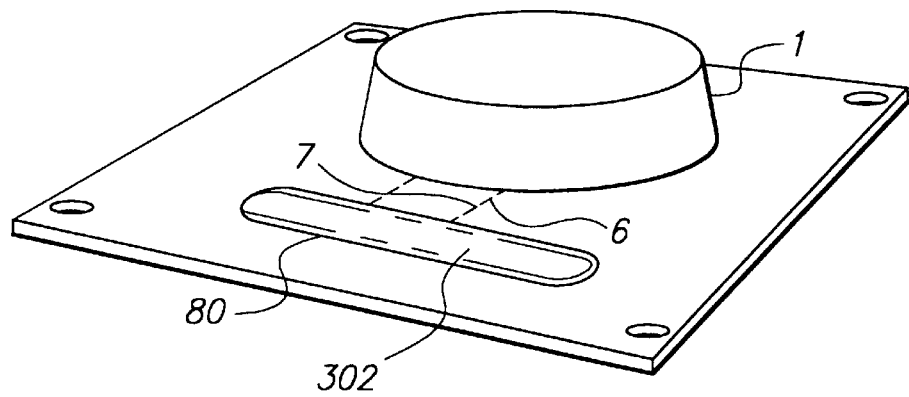
FIG. 5 is a cross-sectional view of a portion of a disposable package of the invention.

As shown in FIG. 6 the convex shape that the flexible porous membrane of the nozzle 302 takes on during use plays an important role. The membrane of the nozzle 302 may be rigid and convex; a nozzle 80 having a rigid convex membrane is shown in FIG. 5. Preferably, the upper surface of the flexible porous membrane of the nozzle 302 is substantially flush with (i.e., in substantially the same plane as) the inner surface of the channel 11 to allow air to flow freely. Thus, if the membrane of the nozzle 302 remained in place when the formulation 5 moved through the pores, the formulation would be released into the slow moving or substantially "dead air" below the boundary layer 13. However, when the formulation 5 is forced from the container 1 by force applied from a source such as a motor-driven cam 22, the formulation 5 presses against the flexible porous membrane of the nozzle 302 causing the porous membrane to convex outward beyond the plane of the resting surface of the nozzle's membrane 302 and beyond the plane of the inner surface of the channel 11. The convex upward distortion of the membrane of the nozzle 302 is important because it positions the pores of the membrane beyond the boundary layer 13 (shown in FIG. 6) into faster moving air of the channel 11.

When pores of the nozzle 302 are positioned beyond the boundary layer into the faster moving air of the channel advantages are obtained. Specifically, the (1) formulation exiting the pores is moved to an air stream where it can be readily carried to the patient and (2) the particles formed do not exit into slow moving or "dead" air and thus do not rapidly decelerate to a degree such that particles behind them catch up with, collide into and merge with the particle. Particle collisions are not desirable because they (a) result in particles which are too large and cannot be efficiently inhaled into the lung (e.g., through agglomeration of particles); and (b) result in an aerosol with diverse and unpredictable particle sizes.

More specifically, when formulation exits the pores the formulation naturally forms spherical particles. Those particles slow down due to the frictional resistance created by the air through which the particles must travel. The particles behind them can face reduced air friction because the preceding particles have moved the air aside. Thus later released particles catch up with and merge into the earlier released particles. This can cause a chain reaction resulting in the formation of large particles which are not suitable for delivery, e.g., can not be readily inhaled into the lung and/or have a diameter of more than about 12.0 microns. Thus (a) or (b) or both phenomena can result in erratic dosing.

A device similar to the device 40 of FIG. 6 can be similarly used to deliver a drug to the respiratory tract by nasal delivery. For example, the mouthpiece 30 and opening 38 are suitably modified to provide for delivery by nasal inhalation. Thus, the patient places the opening of the modified device into his nostril and, after inhalation, a dose of the drug is delivered to the respiratory tract of the patient in a manner similar to that described above.

Aerosol delivery of a drug to the eye can be accomplished using a device similar to the device 40 described above, with modifications. For example, the device 40 shown in FIG. 6 is modified such that the mouthpiece 30, opening 38, and channel are suitable for aerosol delivery to the surface of the patient's eye. The patient positions the device so that aerosol formulation exiting the opening 38 will contact the eye's surface; the channel is open at the opening end (opening 38) and is preferably closed at the end opposite the opening end. The device may additionally comprise a means to maintain the device in a stable position over the patient's eye and/or a means for detecting when the patient's eye is open. Upon activation of the device, a cam 9 (or other mechanical component) crushes the collapsible wall 2 of the container 1. The formulation 5 is forced through the low resistance filter 301, into the open channel 6 (breaking the abutment 7 shown in FIG. 2), and against and through the nozzle 302, thereby generating an aerosol which is forced out of the device through an opening so as to come into contact with the surface of the eye.

Use of the Low Resistance Filter and the Porous Membrane with Single-dose and Multidose Containers The present invention uses a low resistance filter and a porous membrane to prevent clogging of the nozzle's porous membrane and to prevent the passage of undissolved particles or drug and/or other undesirable particles from being delivered to the patient. In general, the formulation is released from a container, passed through at least one low resistance filter, and then passed through a porous membrane of a nozzle. An aerosol is formed from the drug formulation when it exits the pores of the porous membrane, and the aerosol is delivered to the patient. Thus, it is important that the formulation pass through the low resistance filter before the formulation passes through the nozzle's porous membrane and before an aerosol is formed from the formulation.

The low resistance filter and the nozzle can be included as components of a disposable package that is composed of a container that serves as a storage receptacle for the drug formulation, a porous membrane, and a low resistance filter positioned between the drug formulation and the nozzle. Such packages and containers as described above.

The low resistance filter and the nozzle can also be provided separate from the drug container and/or the disposable package. For example, the low resistance filter can be provided as a single disposable filter that can be inserted in the proper position between the formulation in the container and a nozzle, which can also be provided as a single disposable unit. The disposable filter and disposable nozzle can be inserted prior to use and can be disposed after each use or after a recommended number of uses.

Figure 7:
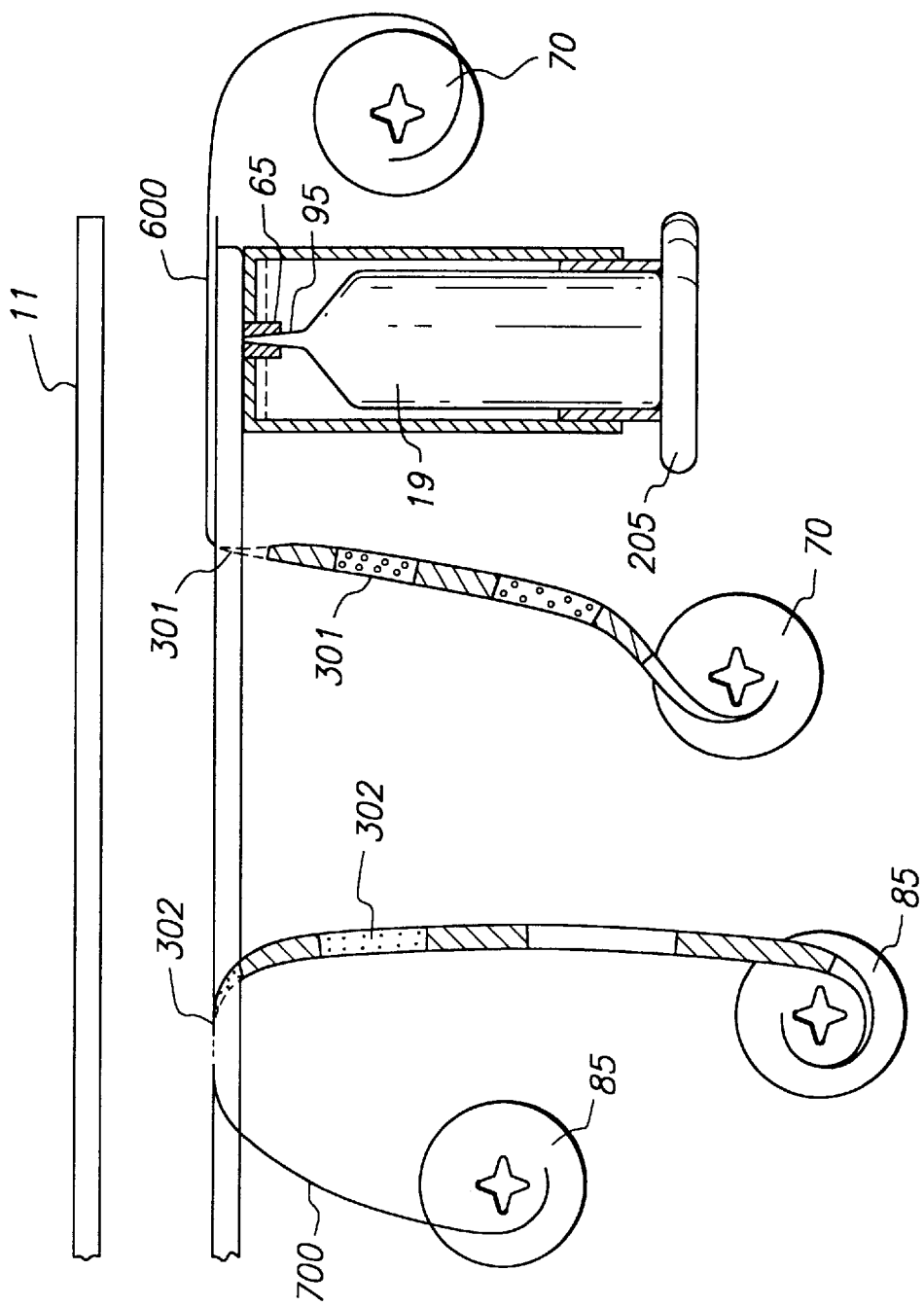
FIG. 7 is a cross-sectional view of an aerosol delivery device of the invention having a multidose container and a ribbon of low resistance filters and a ribbon of porous membranes.
Figure 8:
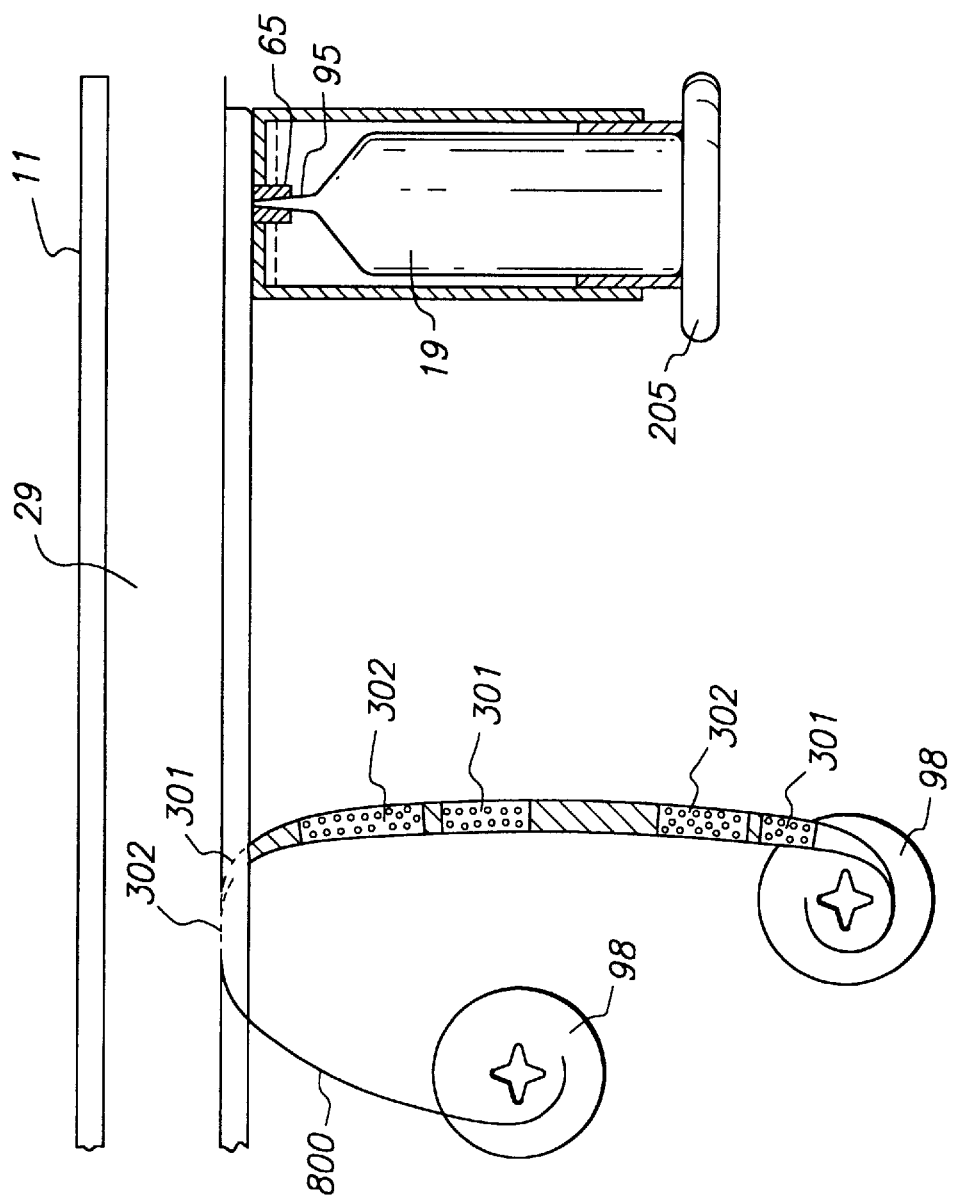
FIG. 8 is a cross-sectional view of an aerosol delivery device of the invention having a multidose container and single ribbon having both interconnected low resistance filters and nozzles comprised of porous membranes.

Alternatively, the low resistance filter and nozzle can be provided as a separate ribbon or ribbons as shown in FIGS. 7 and 8. FIG. 7 shows a cross-sectional view of a delivery device having a multidose container 19. The device is shown with a holder 100 having cylindrical side walls and a removable cap 205. The holder 1 is "loaded" in that it includes a multidose container 1. For example, the multidose container can be a syringe-like device in which the piston of the syringe is used to force a predetermined volume of formulation through the low-resistance filter and nozzle. Alternatively, the multidose container can be a collapsible container that is collapsed in several steps, each collapsing step forcing a specific amount of formulation through the low resistance filter and nozzle to generate an aerosol.

The device additionally comprises a ribbon 600 that comprises a plurality of low-resistance filters 301 that are interconnected to each other and are preferably held in the ribbon 600 in an organized manner, e.g., interfolding or wound, thus making it possible to move the individual filters 301 into a position for filtering the formulation during delivery within the device. In a similar manner, a second ribbon 700 comprises a plurality of nozzles 302 comprised of porous membranes that are interconnected to each other and are preferably held in the second ribbon 700 in an organized manner, e.g., interfolding or wound, thus making it possible to move the individual nozzles 302 into a position for generating an aerosol from the formulation during delivery using the device. Although it is possible to rewind any used portion of the filter ribbon and/or the nozzle ribbon on sprockets 70 and 85, respectively, or randomly fold it into a compartment, it is also possible to dispense the used portion outside of the device 40 and immediately dispose of such. The device can alternatively be configured so that the low-resistance filters 301 are provided in a ribbon 600 as shown in FIG. 7 and the nozzles 302 are provided as a single permanent or disposable portion of the device, or vice versa.

Alternatively, as shown in FIG. 8, the low resistance filter 301 and nozzle 302 can be provided within a single ribbon 800. The low resistance filters 301 and nozzles 302 are interconnected one to another in such a manner that the ribbon 800 is positioned within the device to provide a low resistance filter 301 between the formulation container 1 and a nozzle 302 during delivery of drug or diagnostic agent from the container 1. The ribbon 800 is preferably configured within the device in an organized manner, e.g., interfolding or wound (e.g., on sprockets 98), thus making it possible to move the individual filters 301 and nozzles 302 into a position for filtering and aerosolizing the formulation during delivery.

The formulation may be a low viscosity liquid formulation. The viscosity of the drug or diagnostic agent by itself or in combination with a carrier is not of particular importance except to note that the formulation must have characteristics such that the formulation can be forced out of openings to form an aerosol, e.g., when the formulation is forced through the flexible porous membrane it will form an aerosol preferably having a particle size in the range of about 0.1 to 12 microns for intrapulmonary delivery or in the range of 15 to 75 microns for ocular delivery.

Aerosol Delivery Devices

In general, aerosol delivery devices of the invention are comprised of (a) a device for holding a formulation-containing container, preferably a disposable container, with at least one but preferably a number of containers, and (b) a mechanical mechanism for forcing the contents of a container (on the package) through a low resistance filter and a nozzle comprised of a porous membrane. Where the device is used for respiratory delivery, the device can further comprise (c) a means for controlling the inspiratory flow profile, (d) a means for controlling the volume in which the drug or diagnostic agent is inhaled, (e) a switch for automatically releasing or firing the mechanical means to release a determined volume of aerosol and aerosol-free air after the inspiratory flow rate and/or volume reaches a predetermined point, (f) a means for holding and moving one package after another into a drug release position so that a new package is positioned in place for each release of drug, and (g) a source of power, e.g., spring, or conventional batteries or other source of electric power.

Figure 9:
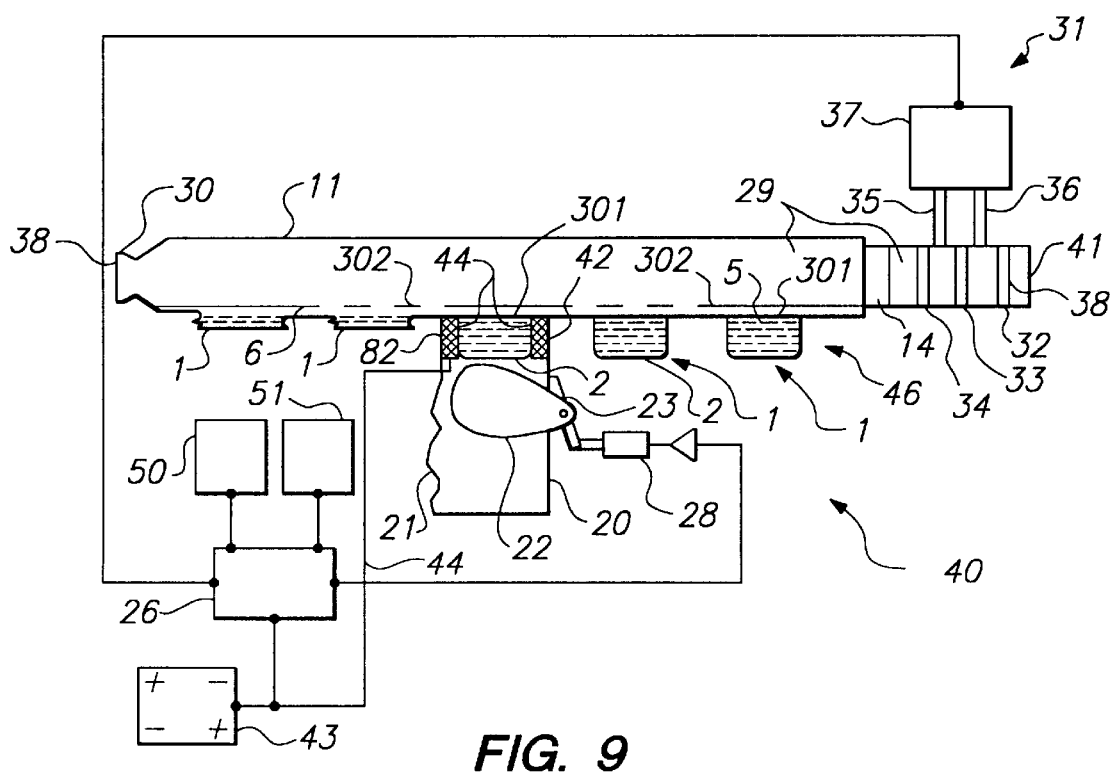
FIG. 9 is a cross-sectional view of an aerosol delivery device of the invention.

The aerosol delivery devices of the invention can also comprise additional components such as, but not limited to, a monitor for analyzing a patient's inspiratory flow (e.g., a flow sensor 31 as shown in FIG. 9 having tubes 35 and 36 connected to a pressure transducer 37, which tubes 35 and 36 communicate with the flow path 29 and which pressure transducer is electrically connected to a microprocessor 26), a heating mechanism for adding energy to the air flow into which the aerosol particles are released (e.g., a heating mechanism 14 as shown in FIG. 9), means for measuring ambient temperature and humidity (e.g., a hygrometer 50 and thermometer 51 as shown in FIG. 9), screens to prevent undesirable particles in the environment from entering the flow path (e.g., screens 32, 33, and 34 as shown in FIG. 9), and/or other components that might enhance aerosol delivery and/or patent compliance with an aerosol delivery regimen. The device can also comprise components that provide or store information about a patient's aerosol delivery regimen and compliance with such, the types and amounts of drug delivered to a patient, and/or other information useful to the patient or attending physician. Devices suitable for aerosol delivery according to the invention (i.e., that can be adapted for use with a low resistance filter and nozzle as described herein) are described in U.S. Pat. No. 5,544,646, issued Aug. 13, 1996; U.S. Pat. No. 5,497,763, issued Mar. 12, 1996; PCT published application WO 96/13292, published May 9, 1996; and PCT published application WO 9609846, published Apr. 4, 1996, each of which is incorporated herein by reference with respect to such aerosol delivery devices.

The methodology of the present invention can be carried out with a device that obtains power from a plug-in source; however, the device is preferably a self-contained, portable device that is battery powered. For example, the methodology of the invention can be carried out using a portable, hand-held, battery-powered device which uses a microprocessor (e.g, as the means for recording a characterization of the inspiratory profile) as per U.S. Pat. No. 5,404,871, issued Apr. 11, 1995, and No. 5,450,336, issued Sep. 12, 1995, incorporated herein by reference. The microprocessor is programmed using the criteria described herein using the device, dosage units, and system disclosed in PCT Application US94/05825 with modifications as described herein. Alternatively, the methodology of the invention can be carried out using a mechanical (nonelectronic) device. Those skilled in the art would recognize that various components can be mechanically set to actuate at a given inspiratory flow rate and at a given volume (e.g., a spinnable flywheel which rotates a given amount per a given volume).

Figure 10:
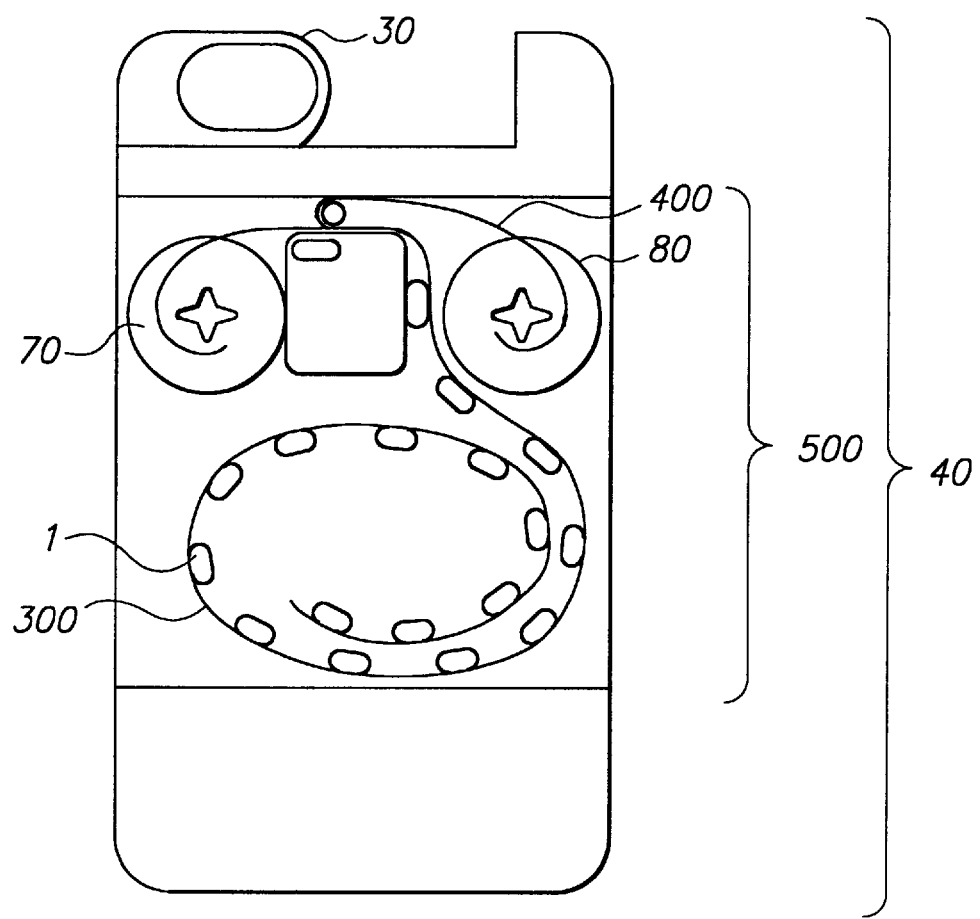
FIG. 10 is a cross-sectional view of an aerosol delivery device of the invention loaded with a cassette.

An exemplary device 40 of the invention is shown in FIG. 9. The device 40 is a hand held, self-contained, portable, breath-actuated inhaler device 40 having a holder 20 with cylindrical side walls and a hand grip 21. The holder 20 is "loaded," i.e., connected to a container 1 that includes dosage units having liquid, flowable formulations of pharmaceutically active drug or diagnostic agent therein. A plurality of containers 1 (2 or more) are preferably linked together to form a package 46. FIG. 10 is a cross-sectional view of a cassette 500 loaded into a delivery device 40. The disposable package 46 is folded or wound into the cassette 500 in a manner which makes it possible to move the individual containers 1 into a formulation release position within the device 40. While the containers 1 are moved into position the cover 400 is removed. Although it is possible to rewind any used portion of the package on a sprocket 70 and rewind the used cover 400 on a sprocket 85 or randomly fold it into a compartment, it is also possible to dispense the used portion outside of the cassette 500 and device 40 and immediately dispose of such.

Although the device 40 shown in FIG. 10 includes a mouthpiece 30 shown here as rotatably attached thereon, it is possible to reconfigure the components so that the mouthpiece 30 is part of and integral with the cassette 500. This arrangement of components makes it possible to dispose of the mouthpiece with the cassette 500 when all the containers 1 on the package 46 have been emptied. The entire device 40 is self-contained and portable. Preferably, the device 40 can be manually actuated and loaded.

In general, any mechanical means for holding the disposable package and applying the necessary force to the collapsible wall to move the formulation through the low resistance filter and through the nozzle's porous membrane to generate an aerosol can be used with the present invention. The device for holding the disposable package can be simply a narrow opening created between two outwardly extending bars 42 and 82 (FIG. 9) or may include additional components for moving new packages into position such as one or more wheels, sprockets or rollers rotatably mounted on the end(s) of such bars. The rollers may be spring mounted so as to provide constant pressure against the surface(s) of the package. The device may also include a transport mechanism which may include providing drive power to the roller(s) so that when they are rotated, they move the package from one container to the next. The power source 43 driving the roller(s) can be programmed via a microprocessor 26 to rotate the rollers only enough to move the package 46 from one container 1 to the next.

Preferably, the mechanical means that applies the necessary force (e.g., less than 50 bar, preferably less than 35 bar) to the collapsible container wall is a cam, e.g., a motor-driven cam. The embodiment shown in FIG. 9 is a simple version of the invention in which the user actuates the device 40 by depressing the actuation mechanism 23, which in turn activates the mechanical force generating means in the form of a motor driven cam 22 (e.g., by activating an electrical activation device 28 which is electrically connected to a power source 43), and the cam 22 is forced against a collapsible wall 2 of a container 1. When the container 1 is compressed its contents are forced out through the low resistance filter 302 through the nozzle 302, and aerosolized. Two additional containers 1 shown to the left are unused. The amount of force sufficient to generate the aerosol is preferably 50 bar or less, more preferably 35 bar or less. The device of FIG. 9 would not require the use of low boiling point propellants such as low boiling point fluorocarbons.

Particle size can be adjusted by adjusting the size of the pores in the nozzle's porous membrane through which the formulation is moved to create an aerosol. If necessary, heat can be added (e.g., using an air-heating mechanism 14 as shown in FIG. 9 and as described above) to evaporate liquid carrier away from aerosolized particles formed.

Particle size adjustment can be used to, for example, target an area of the respiratory tract for aerosol delivery (e.g., deliver formulation to the bronchi, bronchia, bronchioles, alveoli, or circulatory system). A particular area of the respiratory tract can also be targeted by combining particle size adjustment with adjustments in the inspiratory flow rate and the relative volumes of aerosol formulation-containing air and air that does not contain aerosolized formulation that are released. Thus, the device can include some mechanism for completely shutting off inhalation to the patient or giving information to the patient to prompt the correct breathing maneuver. The mechanical device can be an all or nothing mechanism meaning that the flow can be completely free or shut off completely. However, in one embodiment the mechanism provides for a variable flow restriction so that the flow can be completely free to infinitely small. The device may be a ball valve, needle valve or more preferably a gate valve which is closed by the use of a motor or solenoid actuator. Preferably, the mechanism is designed such that it can be moved from a fully opened to a fully closed position in less than 100 at milliseconds and preferably in less than 10 milliseconds.

To use the device 40 for respiratory therapy, a patient (see FIG. 6) inhales air from the mouthpiece 30. The air drawn in through the opening 38 (and optionally a desiccator 41) flows through the flow path 29 of the channel 11. The disposable package 46 is comprised of a plurality of disposable containers 1. Each container 1 includes a drug or diagnostic agent formulation 5 and is covered by the nozzle 302. Where desired, an air-heating mechanism can be located in the flow path 29, and is preferably positioned such that all or only a portion of the air flowing through the path 29 will pass by the heater, e.g., flow vent flaps can direct any desired portion of air through the heater. The heat is preferably turned on for 30 sec or less prior to inhalation and turned off after drug delivery to conserve power.

Particle Size Adjustment

One aspect of the invention involves manipulating the particle sizes in order to target aerosol delivery to, for example, particular areas of the respiratory tract. For example, when it is desirable to deliver drugs (locally or systemically) or diagnostic agents to the outer most peripheral areas of the lung, the method of the present invention involves reducing the particle size to a particle size in the range of 0.5 to 3 microns. When it is desirable to deliver drugs or diagnostic agents to the more central areas of the lung, larger particle sizes can be used and the particle size is adjusted to a size in the range of 2 to 15 microns. In some instances it is desirable to treat both areas simultaneously and to deliver aerosolized drug wherein the particle size is distributed over two different ranges. For example, the particle size could be distributed closely to a size of about 2 microns (within the range of 0.5 to 43 microns) for one group of particles and distributed close to a particle size of about 5 microns (within the range of 3 to 7 microns). The smaller particles would reach and treat, primarily, the peripheral areas of the lungs whereas the larger particles would reach and primarily treat the central areas of the lungs. In some instances, the particle size distribution is kept relatively broad over a range of 0.5 to 9 microns. Alternatively, larger particles can be delivered to the periphery of the lung by slow breathing or small particles can be delivered to the central area of the lung by shallow and/or rapid breathing. In general, larger particles, of a size of 15 to 75 microns, can also be used to accomplish ocular delivery of a formulation.

Aerosol particle size can be adjusted by adjusting the size of the pores of the membrane. In general, for delivery to the respiratory tract, the aerosol is created by forcing the drug formulation through a nozzle comprised of a porous membrane having pores in the range of about 0.25 to 6.0 microns in size, preferably 0.5 to 5.0 microns. When the pores have this size the droplets that are formed will have a diameter about twice the diameter of the pore size. In order to ensure that the low resistance filter has the same or less flow resistance as the nozzle, the pore size and pore density of the filter should be adjusted as necessary with adjustments in pore size and pore density of the nozzle's porous membrane.

Particle size can also be adjusted by adding heat to evaporate carrier. From the period of time from the formation of the aerosolized particles until the particles actually contact the lung surface, the size of the particles is subject to change due to increases or decrease in the amount of water in the formulation due to the relative humidity within the surrounding atmosphere. In order to obtain consistency in terms of the size of particles delivered to the patient regardless of the surrounding atmosphere, it may be desirable to include a component within the aerosol delivery device that adds energy to the surrounding atmosphere (heats the atmosphere) and thereby minimizes the effect of high humidity conditions and reduces the particle size to a minimum consistent size. Alternatively, water vapor can be added to the surrounding atmosphere of the aerosol so that the particles would always enlarge to a maximum consistent size. Detailed information on dynamic particle size adjustment is contained within U.S. patent application entitled "Dynamic Particle Size Reduction for Aerosolized Drug Delivery," U.S. patent application Ser. No. 08/313,461 filed Sep. 27, 1994, which application is incorporated herein by reference in its entirety and specifically incorporated in order to disclose and describe components used in particle size adjustment by the addition of heat to air surrounding the particles. Particle size can also be adjusted by the use of a vibration device which provides, for example, a vibration frequency in the range of about 800 to about 4000 kilohertz. Vibration devices useful in the delivery devices of the present invention are described in U.S. Pat. No. 5,497,763, issued Mar. 12, 1996, and Published PCT Application WO 96/13292, published May 9, 1996, each of which is incorporated herein by reference.

It is desirable to force formulation through the low resistance filter and the porous membrane with a relatively low pressure, e.g., pressure less than 50 bar, preferably pressure less than 35 bar in that lower pressure reduces the chance of breaking the membrane during the release of formulation and makes it possible to make a thinner membrane.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol. In order to aid in avoiding the particle collision problem, it is possible to include a means by which air flow and the flexible membrane of the nozzle 302 prevent collisions. For example, where the device is used for respiratory therapy, the patient inhales, creating an air flow toward the patient over the protruding membrane of the nozzle 302. The air flow carries the formed particles along and aids in preventing their collision with each other. The shape of the container opening, the shape of the membrane covering that opening, as well as the positioning and angling of the flow of air through the channel 11 relative to the direction of formulation exiting the pores of the membrane 302 can be designed to aid in preventing particle collision. It is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangular opening covered by a rigid membrane 80 as shown in FIG. 5. Using such a configuration makes it possible to better utilize the air flow relative to all of the particles of formulation being forced form the pores of the membrane 302. When a circular opening is used, particles which are towards the center of the circle may not be carried along by the air being drawn over the membrane 302 and will collide with each other. The elongated rectangle could be formed in a circle, thereby providing an annular opening and air could be forced outward from the outer and inner edges of the circle formed. Further details regarding such are described in U.S. patent application Ser. No. 08/247,012, filed May 20, 1994, which is incorporated herein by reference to disclose and describe such.

Those skilled in the art will recognize that some adjustments can be made in the parameters such as the size of the pores from which drug is released, vibration frequency, pressure, and other parameters based on the density and viscosity of the formulation keeping in mind that the object is to provide aerosolized particles having a desired diameter.

Firing Point

Where the device is used for respiratory therapy, it is important to note that the firing threshold of the device is preferably not based on a single criterion such as the rate of air flow through the device or a specific time after the patient begins inhalation. The aerosol delivery device preferably comprises a microprocessor that controls the device and takes into consideration the instantaneous (1) air flow rate and (2) the cumulative inspiratory volume. These factors are simultaneously considered in order to determine the optimal point in the patient's inspiratory cycle most preferable in terms of (1) directing medication to a target area of the respiratory tract, (2) reproducible delivering the same amount of drug to the patient with each release of drug, and (3) efficiently delivering drug to the lung. Methods and devices useful in determining an optimal firing point and delivering a drug or diagnostic agent formulation at this optimal firing threshold are described in U.S. Pat. No. 5,497,763, issued Mar. 12, 1996; and PCT Published Application WO 96/13292, each of which is incorporated herein by reference.

Method of Administration and Operation of the Device

The method and device of the invention provides a number of features which make it possible to achieve the controlled and repeatable dosing to particular target areas of the respiratory tract or to the eye required for the treatment of respiratory diseases, ocular diseases, and/or delivery of diagnostic agents. For example, for delivery to the lungs, total lung capacity can be determined and the information used to determine the volumes of air containing aerosolized formulation and air that does not contain formulation to be released. Second, the low resistance filter prevents undesirable particles from reaching the porous membrane to prevent clogging of the porous membrane and to prevent the undesirable particles that may be present in the formulation from being delivered to the patient. Third, the membrane of the nozzle is permanently convex, or is flexible and protrudes into fast moving air aiding the elimination of particle collisions. Fourth, it is possible to eliminate any carrier (e.g., by evaporation) from the aerosolized particles and provide drug to a patient in drug droplets or particles that can be manufactured to have a uniform size. By delivering particles or droplets of a desired uniform size, both the targeting and repeatability of dosing is enhanced. Fifth, the device makes it possible to administer drug at the same point with respect to inspiratory flow rate and inspiratory volume at each drug delivery point thereby improving repeatability of dosing.

The amount of drug or diagnostic agent delivered to the patient will vary greatly depending on the particular drug or diagnostic agent being delivered, as well as whether the drug is to be delivered to or via the respiratory tract or to the eye. In accordance with the present invention it is possible to deliver a wide range of different drugs, including drugs having local and/or systemic effects. For example, where the drug is a respiratory drug (e.g., albuterol, beclomethasone dipropionate, triamcinolone acetonide, flunisolide, cromolyn sodium, salmeterol, formeterol, nedocromil, fluticasone, and ipratropium bromide, including free acids, bases, salts and various hydrate forms of such compounds), the drug is generally administered to a patient in an amount in the range of about 10 $\mu$g to 10,000 $\mu$g. These doses are based on the assumption that when the respiratory delivery methodology is used the efficiency of the delivery is approximately 50% and adjustments in the amount released must be made in order to take into account the efficiency of the device.

The differential between the amount of drug or diagnostic agent actually released from the device and the amount of respiratory drug actually delivered to the patient varies due to a number of factors. For example, where the device is used to deliver drugs to the respiratory tract of the patient, the present device is generally approximately 50% efficient, although the efficiency can be as low as 10% and as high as 90% (e.g., as little as 10% of the respiratory drug or diagnostic agent loaded in the container may actually reach the lungs of the patient). The efficiency of the delivery will vary somewhat from patient to patient and must be taken into account when programming the device for the release of drug. In contrast, a conventional metered dose inhaler device is only about 10% efficient.

When administering drug or diagnostic agent using the device of the present invention, the entire dosing event can involve the administration of anywhere from 10 µl to 10,000 µl, but more preferably involves the administration of approximately 10 µl to 1,000 µl of formulation. Very small amounts of drug or diagnostic agent (e.g., nanogram amounts) may be dissolved or dispersed within a pharmaceutically acceptable, liquid, excipient material to provide a liquid, flowable formulation which can be readily aerosolized. The large variation in the amounts that might be delivered are due to different drug potencies and different delivery efficiencies for different devices, formulations, and patients.

The entire dosing event can involve several inhalations by the patient with each of the inhalations being provided with drug or diagnostic agent from the device. For example, the device can be programmed so as to release the contents of a single container or to move from one container to the next on a package of interconnected containers. Such dosing events comprised of multiple inhalations can be used to, for example, titrate an amount of insulin delivered to adjust the patient's blood glucose level. Delivering smaller amounts from several containers can have advantages. Since only small amounts can be delivered from each container and with a single administration, even a complete failure to deliver drug with a given single dose is not of great significance and will not seriously disturb the reproducibility of the dosing event with multiple administrations.

In addition to the target area of the eye or the desired target area of the respiratory tract, (1) drug potency, (2) delivery efficiency, and (3) sensitivity of the patient to the drug or diagnostic agent must be taken into consideration. The present invention makes it possible to vary dosing over time if sensitivity changes and/or if user compliance and/or lung efficiency changes over time.

Based on the above, it will be understood that the dosing or amount of drug or diagnostic agent (and in particular the volume of aerosolized drug) actually released from the device can be changed based on the patient's responsiveness to therapy or the amount (or adequacy of the amount) of diagnostic agent delivered. For example, where a respiratory drug is delivered according to the invention, the most immediately prior monitoring event wherein the inspiratory flow of a patient's inhalation could be measured. Variations in doses can be calculated by, for example, monitoring the effect of one or more lung function parameters in response to known amounts of respiratory drug released from each container and delivered to the patient. Methods and devices for monitoring lung function parameters in connection with treatment of a respiratory disease or condition by inhalation therapy are described in U.S. Pat. No. 5,497,763, issued Mar. 12, 1996, and PCT Published Application WO 96/13292, published May 9, 1996, each of which is incorporated herein by reference.

Additional information regarding dosing with drugs can be found within Harrison's Principles of Internal Medicine (most recent edition) and the Drug Evaluation Manual, 1993 (AMA-Division of Drugs and Toxicology), both of which are published by McGraw Hill Book Company, New York, incorporated herein by reference to disclose conventional information regarding dosing of drugs and in particular respiratory drugs as well as other useful drugs, diagnostic agents, and formulations.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

What is claimed is:

1. A disposable package for use in aerosolized delivery of a flowable formulation comprising a drug or diagnostic agent, comprising:

a container having at least one wall which is collapsible by the application of a force and having at least one opening, the container having therein a flowable formulation;

a nozzle covering the opening wherein the nozzle is comprised of a porous membrane having pores of a diameter in the range of from about 0.25 micron to about 50 microns; and a low resistance filter positioned between the nozzle and the flowable formulation, wherein the filter has openings, the openings being present at a porosity such that the flow resistance of the filter is substantially the same as or less than the flow resistance of the porous membrane.

2. The disposable package of claim 1, wherein the filter has a porosity that is greater than the porosity of the porous membrane of the nozzle.

3. The disposable package of claim 1, wherein the porosity of the filter is at least 50% porosity.

4. The disposable package of claim 1, wherein the pores of the porous membrane have a diameter in the range of from about 0.25 micron to about 6 microns.

5. The disposable package of claim 1, wherein the pores of the porous membrane have a diameter in the range of from about 5 microns to about 50 microns.

6. The disposable package of claim 1, wherein the force required to collapse the container and aerosolize the formulation is 35 bar or less.

7. The disposable package of claim 1, further comprising a plurality of additional containers wherein each container has at least one wall which is collapsible by the application of a force of 35 bar or less and having at least one opening, and wherein each opening of each additional container is covered with a nozzle comprised of a porous membrane having pores with a diameter in the range of about 0.25 micron to about 50 microns, wherein the additional containers are connected to each other by an interconnecting component.

8. The disposable package of claim 7, wherein the interconnecting component is in the form of an elongated tape.

9. The disposable package of claim 1, further comprising a barrier separating the formulation from the porous membrane, the barrier being rupturable upon the application of force.

10. The disposable package of claim 1, wherein a dry formulation is present in the container, the package further comprising:

an additional container having a flowable liquid therein, the additional container being in a fluid connection with the container having the dry formulation therein.

11. The disposable package of claim 10, wherein the additional container is separated from the container having the dry drug therein by a membrane which is ruptured upon the application of pressure in the amount of 50 bar or less.

12. The disposable package of claim 1, further comprising a removable cover sheet positioned over the nozzle, the cover sheet being held in place by a seal.

13. The disposable package of claim 1, wherein the porous membrane of the nozzle is flexible.

14. The disposable package of claim 1, wherein the porous membrane has a thickness in the range of about 2 to about 20 microns.

15. The disposable package of claim 1, further comprising a burstable seal positioned between the formulation and the nozzle.

16. A method for generating an aerosol for delivery to a patient wherein the aerosol is composed of particles of a desired size, the method comprising the steps of:

applying force to a flowable formulation comprising a pharmaceutically active drug or diagnostic agent;

passing the formulation through a low resistance filter; and passing the formulation through a nozzle comprised of a flexible, porous membrane, the membrane having pores of a diameter in the range of from about 0.25 micron to about 50 microns and having a porosity substantially equal to or less than the porosity of the low resistance filter;

wherein an aerosol primarily composed of a desired particle size is generated.

17. The method of claim 16, wherein the formulation is a flowable liquid.

18. The method of claim 16, wherein the formulation is contained in a disposable container.

19. The method of claim 18, wherein the disposable container has at least one collapsible wall and at least one opening.

20. The method of claim 16, wherein the formulation is contained in a multidose container.

21. The method of claim 16, wherein the force applied to the formulation is 35 bar or less.

22. The method of claim 16, wherein the porosity of the low resistance filter is as low as about $10^{-4}\%$ to about 1%.

23. The method of claim 16, wherein the force is applied by means of a motor-drive cam.

24. A method for delivering an aerosolized volume of air to a target area of the respiratory tract of a patient, comprising:

drawing air through a channel and over a surface of a flexible, disposable nozzle, and into the respiratory tract of a patient, wherein the nozzle is comprised of a porous membrane having pores with a diameter in the range of about 0.25 to about 50 microns;

measuring the volume of air inhaled by the patient;

after a measured volume of air is inhaled, applying force to a flowable formulation comprising a carrier, and a drug or diagnostic agent, said force being sufficient to extrude the formulation through the openings of a low resistance filter and through the pores of the porous membrane to create an aerosolized volume of air;

drawing a measured volume of aerosolized air through the channel and into the lungs of to the patient.

25. The method of claim 24, wherein the low resistance filter has a porosity substantially the same as or greater than the porosity of the porous membrane.

26. The method of claim 24, wherein the formulation is contained in a container of a disposable package, the container having at least one wall which is collapsible by the application of said force.

27. The method of claim 24, wherein the formulation is contained in a multidose container.

28. The method of claim 24, wherein the force applied to the formulation is 35 bar or less.

29. The method of claim 24, wherein the force is applied by a motor-driven cam.

30. An aerosol delivery device, comprising:

a channel having an opening for delivery of an aerosol to a patient;

a drug formulation container containing a drug formulation, the container being positioned for delivery of the formulation into the channel;

a means for applying physical force to the drug formulation container upon actuation;

a flexible, disposable nozzle comprised of a porous membrane, the nozzle being positioned between a formulation container and the channel, wherein the porous membrane has pores having a diameter in the range of from about 0.25 micron to about 50 microns; and a low resistance filter positioned between the nozzle and the formulation container, the low resistance filter having openings, the openings being present at a porosity equal to or greater than the porosity of the porous membrane;

wherein the device is a hand-held self-contained device having a total weight of 1 kilogram or less.

31. The device of claim 30, wherein the channel opening is adapted for withdrawal of air by a patient, the channel additionally comprises an opening into which air can be inhaled, and the pores of the porous membrane have a diameter in the range of from about 0.25 micron to about 6 microns.

32. The device of claim 31, wherein the device further comprises a means for measuring the volume of aerosolized and aerosol-free air.

33. The device of claim 30, wherein the pores of the porous membrane have a diameter in the range of from about 5 microns to about 50 microns.

34. The device of claim 30, wherein the drug formulation is contained in a multidose formulation container.

35. The device of claim 30, wherein the drug formulation is contained in a disposable package, wherein the package comprises a formulation container having at least one wall which is collapsible by the application of the physical force.

36. The device of claim 30, wherein the mechanism applies a physical force of 35 bar or less upon actuation.

37. The device of claim 30, wherein the means for applying force is a motor-driven cam.

38. The device of claim 30, wherein the low resistance filter is contained in a ribbon having interconnected low resistance filters.

39. The device of claim 30, wherein the porous membrane is contained in a ribbon having interconnected nozzles.

40. The device of claim 30, wherein the low resistance filter and the porous membrane are contained in a ribbon having interconnected low resistance filters and nozzles.

* * * * *